(12) United States Patent
Guenther et al.

(10) Patent No.: US 7,345,759 B2
(45) Date of Patent: Mar. 18, 2008

(54) METHOD AND DEVICE FOR THE MEASUREMENT OF CHEMICAL AND/OR BIOLOGICAL SAMPLES

(75) Inventors: Rolf Guenther, Hamburg (DE); Leif Brand, Remscheid (DE); Christian Eggeling, Goettingen (DE); Karsten Gall, Lunestedt (DE); Claus Seidel, Haan (DE)

(73) Assignee: Evotec OAI AG, Hamburg (DE)

( * ) Notice: Subject to any disclaimer, the term of this patent is extended or adjusted under 35 U.S.C. 154(b) by 253 days.

(21) Appl. No.: 10/380,192

(22) PCT Filed: Aug. 22, 2001

(86) PCT No.: PCT/EP01/09680

§ 371 (c)(1),
(2), (4) Date: Dec. 16, 2004

(87) PCT Pub. No.: WO02/16911

PCT Pub. Date: Feb. 28, 2002

(65) Prior Publication Data

US 2005/0164160 A1 Jul. 28, 2005

(30) Foreign Application Priority Data

Aug. 22, 2000 (DE) ................................ 100 40 988

(51) Int. Cl.
*G01N 21/64* (2006.01)
(52) U.S. Cl. ...................................... 356/317
(58) Field of Classification Search ..................... None
See application file for complete search history.

(56) References Cited

U.S. PATENT DOCUMENTS 5,784,157 A 7/1998 Gorfinkel et al.
6,826,422 B1 * 11/2004 Modell et al. ............... 600/407

FOREIGN PATENT DOCUMENTS

| DE | 196 34 873 A1 | 3/1998 |
| DE | 197 18 016 A1 | 11/1998 |
| WO | WO94/16313 A2 | 7/1994 |
| WO | WO96/27798 A1 | 9/1996 |

OTHER PUBLICATIONS

C. Zander et al., *Detection and Characterization of Single Molecules in Aqueous Solution*, Appl. Phys. B 63, pp. 517-523 (1996).

* cited by examiner

*Primary Examiner*—Tu T. Nguyen
(74) *Attorney, Agent, or Firm*—Griffin & Szipl, P.C.

(57) ABSTRACT

A device for the measurement of chemical and/or biological samples, in particular by means of luminescence spectroscopy, comprises an irradiation unit, a sample receiver, at least one optical unit and a detector unit. The color marker in the sample, which contains at least one color marker, is stimulated by irradiation into producing luminescence and gives off light. The light emitted by the color markers is detected by detectors in the detector unit. According to the invention, the measurement results may be improved by the irradiation unit generating pulsed irradiation. The irradiation unit is thus preferably controlled by a control unit in such a way that the irradiation pulses impinge on the sample in a temporal sequence.

38 Claims, 4 Drawing Sheets

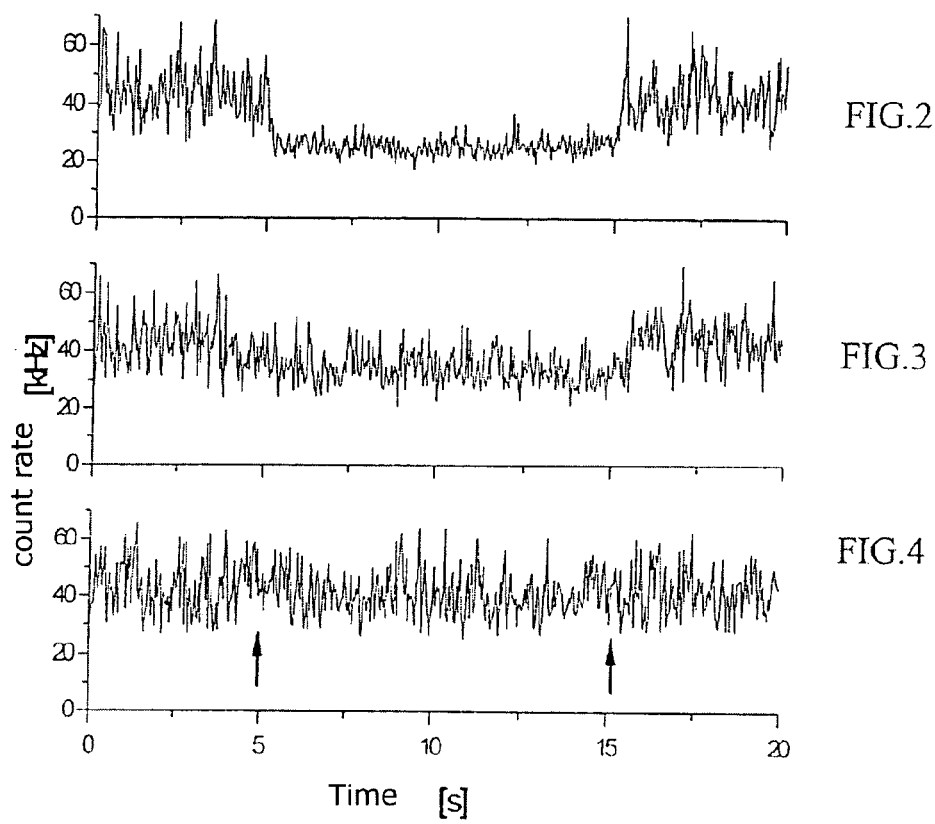
FIG.2
FIG.3
FIG.4
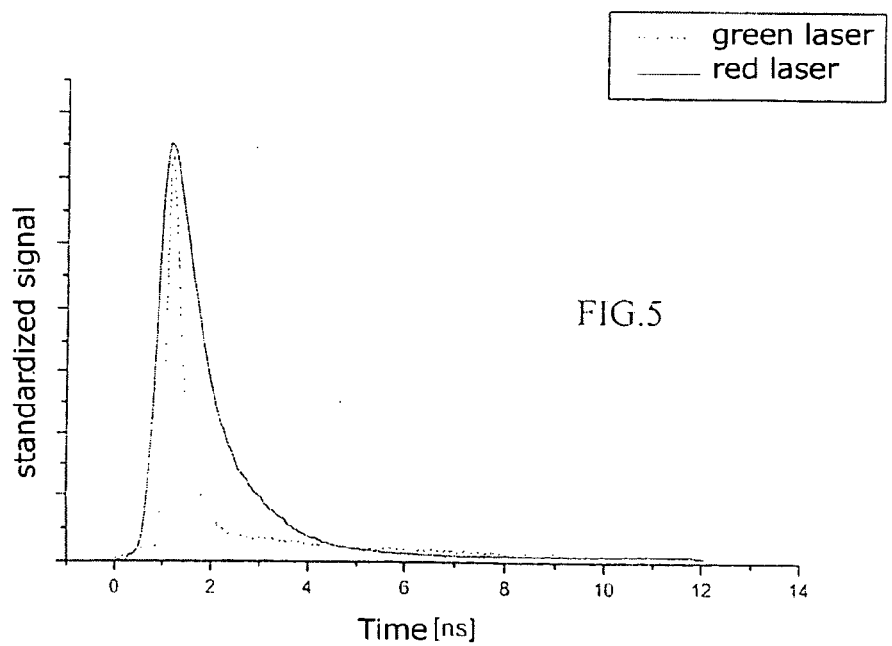
FIG.5

METHOD AND DEVICE FOR THE MEASUREMENT OF CHEMICAL AND/OR BIOLOGICAL SAMPLES

This is a National Phase Application in the United States of International Patent Application No. PCT/EP01/09680 filed Aug. 22, 2001, which claims priority on German Patent Application No. 100 49 988.1, filed Aug. 22, 2000. The entire disclosures of the above patent applications are hereby incorporated by reference.

BACKGROUND OF THE INVENTION.

The invention relates to a method and device for the measurement of chemical and/or biological samples, in particular with the use of luminescence spectroscopy.

A known method for the measurement of such samples is the screening of the samples. In screening, the interaction between two bio-molecules in the presence of a test substance is studied. The bio-molecules can be, for example, the pairs of ligand-receptor, substrate-enzyme, protein-protein, or protein-DNA. A measurable signal may be produced either by the bio-molecules themselves, or, as in most cases, sample markers have to be bound to the bio-molecules. As markers, substances are employed that produce signals based on radio activity, luminescence or absorption. When color markers are used that produce luminescence, the color markers are excited by electromagnetic radiation, e.g. suitable laser light, so that the electromagnetic radiation lifts an electron to a higher energy level and the color marker gives off light, i.e. luminesces, by the electron returning to its original energy level. The probability of the return of the electron to its original energy level, and thus of the emission of luminescence, is exponentially distributed overtime. The mean duration of the exited state is therefore also referred to as the luminescence life. Since, in most cases, luminescent markers have but a slight influence on the interactions between bio-molecules and are extremely sensitive compared to other markers, the use of luminescent color markers is particularly advantageous. Information on reactions between two bio-molecules are obtained by establishing a relation between the change in the light emitted by the color markers and the reaction of the bio-molecules.

In an example of a measuring method, a target molecule is first exposed to a fluorescent reagent as a luminescent reagent adapted to bind to the target molecule. If, for example, the intensity of the fluorescence changes during the binding, it can be used to quantify the binding. In another experiment, the target is exposed to both the fluorescence-marked reagent and a single substance. If a binding between the substance and the target occurs, the fluorescence-marked reagent is separated from the target. Thus, the ratio of bound and free marked molecules changes. In turn, this entails a change in the emission of fluorescence by the sample and it can be assessed whether and in how far a substance binds to the target.

In order to increase the amount of information to be acquired during a measurement, a plurality of markers, in particular two color markers, may be used. Depending on the excitation energy of the two color markers, two electromagnetic radiation sources, e.g. lasers, of different wavelengths are employed to excite the color markers. For example, a red and a green color marker is used in combination with a red and a green laser. When red and green color markers were used, it has been found that, when a red laser was used together with a green laser, the intensity of the light emitted by the red color marker is less than the intensity of the red color markers, when the same is irradiated exclusively with red laser light. This loss of intensity entails a loss of information and leads to falsified results.

This phenomenon can also be found when color markers of different colors are used.

BRIEF SUMMARY OF THE INVENTION

It is the object of the invention to provide a method and device for the measurement of chemical and/or biological samples, in particular with the use of luminescence spectroscopy or microscopy, by which improved results can be obtained. In particular, it is the object of the invention, to achieve an improvement of the measured results for commonly used red and green color markers.

The object is solved according to the invention with a method and device as described herein.

According to the invention, an improvement of the measured results can be achieved by pulsing the electromagnetic radiation used to test the samples at least in a wavelength range and/or at least one polarization. A measuring volume of the sample including at least one color marker is irradiated with electromagnetic radiation of at least two different wavelengths/wavelength ranges and/or polarizations, the radiation being pulsed in at least one wave-length/wavelength range and/or at least one polarization. Specifically, it is possible to provide for a relative movement between color marker and measuring volume during a relative movement time; in this case, it is desirable to pulse the radiation such that at least two radiation pulses impinge on the color marker per relative movement time.

Pulsating one or a plurality of wavelength ranges and/or one or a plurality of polarizations, is preferably effected such that at least two radiation pulses impinge on the color marker within a time during which the marker diffuses through the measuring volume. The measuring volume, which in high-throughput screening preferably corresponds to the focal point of an irradiation optic, is preferably smaller than $10^{-9}$ l, in particular smaller than $10^{-12}$ l. A particle, such as a molecule, provided with a color marker diffuses through the measuring volume. According to the invention, the time interval between successive pulses is chosen such that a particle diffusing through the measuring volume is hit by at least two radiation pulses and the color marker is excited to luminesce at least twice. In this case, the relative movement time corresponds to the diffusion time of the marker through the measuring volume.

In another embodiment, a stationary marker (e.g. a marked immobilized macro-molecule, a marked sedimented or adherent cell, etc.) may be examined, the relative movement being effected in particular by a stepped movement of the measuring volume. This scanning process can be performed either by moving the sample with the exciting beam path being stationary or by scanning the sample by varying the position of the exciting beam path. In this case, the relative movement time corresponds to the time required to move the measuring volume along the marker or to move the marker through the measuring volume by moving the sample. The scanning could also be continuous, this embodiment eventually corresponding to a step-wise scanning in infinitesimally small steps.

Of course, any intermediate form is conceivable between these extremes, such as scanning slowly diffusing markers or using a parallelized optic configuration (e.g. by using a plurality of optical fibers (a fiber bundle)) to simultaneously produce several measuring volumes.

Typical diffusion times of particles through the measuring volume are within the range of 50 µs to 100 ms, in particular 2 ms to 10 ms. The interval between successive radiation pulses is preferably chosen as short as to have the individual particles preferably be hit by at least 100 radiation pulses even with diffusion times that short. It is most preferred to have at least 1,000 and in particular at least 5,000 radiation pulses hit during the diffusion through the measuring value. Because of the high number of radiation pulses, the electrons of the color markers are raised to higher energy levels several times, therefore giving off photons several times while falling back to their original level. The more light is emitted from a color marker bound to a particle, such as a molecule, the more information can be acquired within the diffusion time.

This allows for an increase in the expressiveness of the information obtained. Similarly, it is also desirable to provide a high number of radiation pulses during the other above-mentioned possible relative movement times. In one embodiment of the present method, such a radiation pulse could be sub-pulses as they are known from multi-photon excitation, in particular dual-photon excitation, to excite a luminescence emission by the color marker.

When using electromagnetic radiation, for example, with two different wave-length ranges, for example, such as red and green laser light, the red or green laser light continuously irradiates the sample and the respective other laser light is pulsed. When using red and green laser light, preferably the green laser light is continuous and the red laser light is pulsed. The luminescence signal caused by a pulsed excitation has a characteristic course in time, the intensity decreasing over time after one excitation to the next excitation. The course in time of a pulsed excitation is thus known with sufficient exactness. The excitation and the emission of the color markers excited by the other wavelength range have a continuous course in time. Both luminescence signals emitted by the sample are thus discernible by their different courses in time.

It is thus possible to significantly improve the measured results by pulsing a light source. Since laser light of different wavelengths is emitted and only one of both laser light sources has to be pulsed, when two laser light sources are used, this is a simple and economic modification of the device required to practice the method. Specifically, it is advantageous in the above example to pulse the red laser, since green pulsed lasers are still very costly today. Otherwise, a combination of all wavelengths tuned to the color markers to be examined is possible, the use of at least two different wavelengths between 350 nm and 800 nm being preferred. Moreover, in another embodiment of the present method, the use of UV laser diodes would be possible. Another advantage of the present method is that only one detector is needed to detect the two luminescence signals emitted by the sample.

Of course, the present invention can also be applied for more than two different wavelength ranges. It is likewise possible to use different polarizations of the radiation exciting the color markers, instead of using different wavelength ranges. Similarly, an improvement of the measured results can be achieved with the above present method if only one color marker is employed, since the same is excited differently by radiation of different wavelength ranges and/or different polarizations, for example, so that different sets of information can be obtained.

Among other things, the invention is based on the fact that a red color marker excited by red laser light could be destroyed by green laser light. The destruction is caused by an electron of the red color marker is raised to a higher energy level by the red laser light and is further excited by the green laser light. This excitation by the green laser leads to an increase in the probability of the destruction of the red color marker, e.g. by ionization. In most cases this destruction is irreversible, i.e. the color marker can no longer be excited to emit luminescence and is lost for further measurement. This causes a deterioration in the measuring signal. This is also true for color markers of other colors.

In a particularly preferred manner, a further inventive improvement of the measuring signal can be achieved by pulsing the radiation used to examine the samples, such as the laser light, and by using electromagnetic radiation having at least two different wavelength ranges and/or polarizations that are given off in a deferred manner. Here, the pulsing is effected in at least two wavelength ranges and polarizations, respectively. The electromagnetic radiation of different wavelength ranges and/or different polarizations thus impinges successively on the sample. For example, the risk of a destruction of the color marker is reduced by the fact that the radiation pulse that could destroy the color marker impinges at a moment in time in which it highly probable that the excited electron has already returned to its original state.

By pulsing the electromagnetic radiation in all wavelength ranges and/or both polarizations, further improvements of the measured results can be obtained.

An improvement of the measured results can be obtained by the above inventive method even if only a single color marker is present in the sample. This color marker is excited differently by the electromagnetic radiation of different wavelength ranges and/or different polarizations. For example, different polarizations can be detected in the emitted radiation, allowing to draw conclusions on the rotational properties of the color markers.

The terms color substance marker/color marker/marker refer to both a marker supplied to the sample (such as rhodamine, oxazine, cyanine or another color substance) and a marker inherent to the substance to be examined, i.e. substances that preferably have luminescent properties, such as certain bio-polymers. The terms color substance marker/color marker/marker also refer to other substances that may be examined using spectroscopic or microscopic methods such as Raman scattering. Luminescence particularly also includes fluorescence and phosphorescence.

The term wavelength range used herein also includes, besides wider excitation wavelength ranges typically extending over a plurality of nanometers, more discrete wavelengths. In particular, it may be desired to provide a monochromatic excitation for at least two different wavelengths.

In the following, the invention will first be discussed with reference to the use of electromagnetic radiation with different wavelength ranges. For a better understanding, this is done with reference to an example including a red and a green color marker, each being excited by red and green laser light, respectively.

According to the invention, the laser light, i.e. the red and the green laser light in the example discussed, is pulsed to excite the color markers. In addition, the laser light pulses of the individual wavelength ranges are deferred in time relative to each other. Due to the time-synchronized temporal offset of the pulses relative to each other, the sample is always hit only by either a red or a green laser light pulse at any moment. Even with an extremely small interval between the green laser light pulse and the red laser light pulse, substantially fewer red color markers are destroyed. This increases the intensity or the count rate of the light given off by the color markers. Thus, the measuring results can be improved significantly.

According to the invention, when using red and green color markers, first, one or a plurality of light pulses of the red laser light and, subsequently, one or a plurality of light pulses of the green laser light are directed to the sample. A time gap exists between the last red light pulse and the first green light pulse. The time span is chosen such that the excitation of the red color markers has substantially decayed again so that the electrons of the red color marker are not further excited from a high energy level by the green laser light pulse and the red color markers will not be destroyed in the course.

Preferably, in the present method, a laser light pulse is generated only after the substantial decay of the excitation of the color marker excited by previous laser light pulse of a different wavelength range. Thus, for example, the green laser light pulse is directed to the sample only when the excitation of the color markers excited by the red laser light pulses has decayed substantially. Preferably, the next laser light pulse is fired on the sample only when the excitation of the previously excited color marker has decayed by at least 90%, more preferably by at least 95%, most preferably by at least 98%. Hereby, the measuring results obtainable are significantly improved.

The necessary temporal offset of two successive light pulses of different wavelength ranges depends on the luminescence life of the color marker used. For a color marker with a life of 3 ns, the necessary temporal offset is at least 2 ns, preferably at least 7 ns. For a life of 1 ns, it is at least 0.7 ns, preferably at least 2.3 ns. Pulses with different intensities can be used, which is also true for non-luminescent excitation. When a red and a green laser light are used, the distance between a green laser light pulse following a red laser light pulse and a red pulse is crucial, since a green laser light pulse emitted too early or simultaneously with the red laser light pulse could cause the destruction of the red color marker. However, the temporal offset between a red laser light pulse following a green laser light pulse and a green pulse is of no importance, since the green color marker is not destroyed by the red laser light pulse. In this case, it should merely be ensured that both pulses do not occur at the same time.

The pulse length of the individual radiation pulses impinging on the measuring volume is preferably smaller than 1 ns. In particular, the radiation pulses are smaller than 500 ps and, more preferred, smaller than 300 ps. The pulse length specifically depends on the time deferment of successive pulses. Here, as stated above, it has to be made sure, according to the invention, that the excitation of a color marker has substantially decayed. When modern lasers are employed, it is even possible to achieve pulse widths smaller than 10 ps.

For fluorescence excitation, the pulse frequency of the laser light preferably is 20-100 MHz, more preferably 60-80 MHz. The pulse frequency of the individual laser light ranges are preferably identical so that the distances between the successive laser light pulses of different wavelength ranges and/or polarizations remain constant over time.

Preferably, the sequence of the laser light pulses of the individual wavelength ranges and polarizations is repetitive. For example, when three lasers with different wavelength ranges are used, a light pulse is sent to the sample first by the first, then by the second and thereafter by the third laser, whereafter the first laser again emits a pulse, followed by the second laser, and so on. When two lasers are used, e.g. a red and a green laser, the laser light pulses are preferably generated alternately.

According to the above described preferred embodiments of the invention with reference to the use of laser light and the laser light pulses generated according to the invention, the same inventive effect is caused when other electromagnetic radiation, such as radiation in the invisible wavelength range, is used. Corresponding radiation pulses have the same effect as laser light pulses. Likewise, it is possible with the above described embodiments, to use a sample with only one color marker. This one color marker is excited differently by radiation pulses of different wavelength ranges, the emitted radiation being different or possibly being different depending on the wavelength ranges of the exciting radiation.

It is also possible to employ different pulse frequencies of common multiples (e.g. 40 MHz and 80 MHz). A constant offset in time between the two laser light pulses would still be ensured. This is advantageous, if one of the two lasers, e.g. the red laser, has less power. Since the intensity of the luminescence emission is proportional to the excitation power, a pulse frequency of the green laser (e.g. 40 MHz) reduced by half with respect to the red laser (e.g. 80 MHz) can result in a comparable intensity of the luminescence emission by the red and the green color marker. Despite the lower excitation power, the red color marker is excited twice as often. In particular, the invention also provides for detection with the use of Raman scattering instead of luminescence effects (luminescence spectroscopy and luminescence microscopy). In this case, excitation sources with particularly high repetition rates can be used because of the instantaneous emission of the Raman photons. Here, it is particularly advantageous, to exploit surface-amplified Raman emission, since the effective cross section and, thus, the number of emitted photons is particularly high. The conventional methods for exploiting the surface-amplified Raman emission, such as the metallizing of surfaces, especially particle surfaces, with silver, can be applied here.

The present method using two or more pulsed electromagnetic beams of different wavelength ranges, offers a plurality of possible applications in the field of transient spectroscopy, such as the transient absorption spectroscopy (TRABS). For example, when using two pulsed laser light sources, all color markers are excited by the first laser light pulse. The second, deferred laser light pulse selectively saturates or photo-destroys certain color markers or fluorescent impurities. Hereby, a controlled lowering of fluorescence signals can be achieved and specific color markers may be made preferred or discernible. It is possible to employ a plurality of deferred pulses in different wavelength ranges, instead of time pulses with different wavelength ranges, the respective wavelength ranges being selected such that certain color markers are saturated or photo-destroyed.

Results, corresponding to those obtained with the use of different wavelength ranges, may also be obtained with different polarizations of the electromagnetic beams. For example, instead of using red and green lasers, similar measuring results can be obtained with the use of vertically and parallel polarized light that also allows to make statements on the substance examined.

The wavelength range of green laser light used preferably ranges from 480-550 nm, more preferred 485-535 nm. The wavelength range of a red laser preferably ranges from 630-690 nm, more preferred 535-655 nm. Preferred possible green laser light sources are high-quality argon ion lasers with monochromatic excitation at 488 nm, 466 nm, 502 nm, 515 nm, 528 nm, or Nd:YAG Lasers with monochromatic excitation at 492 nm or 532 nm. Red laser light sources preferably are krypton lasers with monochromatic excitation at 647 nm, such as red laser diodes available for various excitation wavelengths.

Often applied methods using two color markers with two lasers of different colors are coincidence analyses discussed here with reference to fluorescence. Here, it can be determined in how far the color markers occur simultaneously or separately, i.e. to what degree they are bound to a common reagent or to two separate reagents. This makes use of the fact that in case of a simultaneous occurrence the fluorescent light of both colors is detected at substantially the same time, while in case of a separate occurrence, the detection of the fluorescent light of both colors is randomly distributed over time. Again, the example of red an green may serve to explain this. A special case of coincidence analysis is the cross correlation analysis. Here, the fluctuations over time of the fluorescent light of one color marker, $F_{green}(t)$, are registered by a second detector detecting those of the other color marker $F_{red}(t)$. The cross correlation function $G(t_c)$ is calculated based on these fluctuation traces.

$$G(t_c) = \frac{< F_{green}(t) F_{red}(t + t_c) >}{< F_{green}(t) > < F_{red}(t) >} \quad \text{Eq. 1}$$

(t: measuring time, $t_c$: correlation time, < ... >: averaging over t)

A cross correlation function not equal to zero will only be obtained, if the fluorescent lights of both color markers are connected ("correlated") with respect to time. This is true when they are bound to a common reagent. The amplitude of the cross correlation function, $G(t_c=0)$, allows for a direct statement on the concentration, $C_{green+red}$, of this twice color-marked reagent compared to the concentrations, $C_{green}$ and $C_{red}$, of the once marked reagents ($C_{green}$ and $C_{red}$ can be determined by other analytic methods).

$$G(t_c = 0) = \frac{C_{green+red}}{(C_{green} + C_{green+red})(C_{red} + C_{green+red})} \quad \text{Eq. 2}$$

By the already mentioned destruction of the color markers, an undesired reduction of the concentrations, $C_{green+red}$, of the twice color marked reagent (and of $C_{red}$, the red marked reagent) and, thus, a decrease of the cross correlation amplitude, $G(t_c=0)$ occurs. Such an analysis of a biological system by cross correlation would lead to falsified results and underestimate the actual biological concentration of the twice color marked reagent, $C_{green+red}$. Therefore, the invention provides for a temporal offset between the red and the green laser light pulses. By preventing the red color marker from being destroyed, this disadvantageous influence on the correlation amplitude is canceled out and a true cross correlation or coincidence analysis is obtained.

Another problem with measuring methods using two color markers with two lasers of different colors is the cross-talk of the luminescence signal of both color markers. This will be explained with reference to fluorescence. The absorption and emission spectra of fluorescent colors are comparatively wide, i.e. they extend over a relatively large wavelength range, and they may overlap. This may cause the following problems that do not allow for an unambiguous attribution of the fluorescent light to a particular color marker or excitation laser—e.g., they could lead to falsifications in the cross correlation function. These will again be explained with reference to red and green:

i) the fluorescent light of the red color marker may also be excited by the green laser (in a restricted manner)—the red fluorescent light excited by the green laser and the red laser, respectively, overlap;

ii) a (small) part of the fluorescent light of the green color marker overlaps with the red fluorescent light ("crosstalk")—an overlapping of the fluorescent light emitted by the green and the red color markers occurs on the detector for the red radiation;

iii) the fluorescent light of the red color marker may be generated not only by the red laser, but also—through resonance energy transfer—by the green color marker excited by the green laser—similar to the case i), an overlapping of the red fluorescent lights excited by the red laser and, indirectly through energy transfer, by the by the green laser.

It is the intention of the invention, to prevent this crosstalk of the fluorescence signals by deferring the red and green laser light pulses relative to each other. The fluorescent light excited by the green and the red laser can then be separated with respect to time and allows for an unambiguous attribution, as can be explained with reference to the three problem cases: after the green laser light signal, only the portion of the green color marker (suppression of the "crosstalk") or of the red color marker in the red fluorescent light, the red color marker being excited directly or indirectly by energy transfer. If, after decay of this fluorescence, the red laser light pulse follows, the red fluorescent light only contains portions of the red color marker excited directly by the red laser. If, however, the green laser is timed to the decay of this fluorescence, the fluorescent light can clearly be attributed to the color markers or the exciting lasers. Thus, an uncompromised cross correlation analysis becomes possible, for example.

A further inventive application of the temporal offset between two laser light pulses is the detection of different polarizations of the luminescent light—in the following referred exclusively to fluorescent light—of a color marker by only one detector. In conventional measuring methods for detecting different polarizations of fluorescent light, the color marker is excited by a laser polarized in a certain plane X and the polarization portion of the fluorescent light parallel and vertical to X is registered either simultaneously on two different detectors with the help of a polarization beam splitter, or, separated in time (several seconds), on a single detector by a timed switching of the transmission direction of a polarization filter. This allows to draw conclusions on the rotational properties of the examined color markers. It is the idea of this invention, to generate time-separated fluorescence signal pulses (decay pulses) of different polarization by two time-separated laser pulses polarized in the plane X and in the plane Y perpendicular thereto (this is possible even with only one laser when split). If the detection is done on a single detector with a polarization filter with a constant transmission direction, a comparable detection of the fluorescent light component parallel and vertical to the polarization plane of the laser may be performed: the transmission direction of the polarization filter is assumed to b the plane X; if the first laser light pulse is emitted with a polarization also in the plane X, the portion of the fluorescent light polarized in parallel to the polarization plane of the laser is then detected; after the decay of this fluorescence, the second laser pulse is emitted with a polarization in the plane Y vertical to the plane X; thereafter, only the portion of the fluorescent light that is polarized perpendicular to the plane X of the laser is detected; after its decay, another laser pulse is emitted with a polarization in the plane X; etc. This detection of the two polarization portions is done almost simultaneously since the delay between the two laser light pulses is restricted only to the decay of the fluorescent light which is within the range of the fluorescence life of the color markers, typically between 1-4 ns. This "simultaneous" detection of both polarizations can therefore be achieved with little material effort using only one detector and one laser, so that it is of great interest for any application employing fluorescence anisotropy and polarization measurement.

In a similar manner, a delay between the red and the green laser allows for a "simultaneous" detection of the red and the green luminescence signal on only one detector with a delay in the range of ns.

Thus, the present method allows for a two color cross-correlation analysis with only one detector.

To obtain particularly good measuring results when using different wavelength ranges and/or polarizations, it is preferred to employ a high-sensitive confocal microscope.

Another advantageous possible application of the present method lies with analyses employing fluorescence resonance energy transfer (FRET). In FRET analyses of chemical and/or biological samples, advantage is taken of the fact that the excitation energy of a substance (donor), previously excited with a particular wavelength, can cause luminescence of another substance (acceptor). The acceptor is thus additionally or exclusively excited by energy emitted from the donor (energy transfer). The effectiveness of this energy transfer is extremely dependent on the spatial distance and the spatial orientation of the donor and the acceptor, so that variations in the distance between these two substances can be studied very effectively using FRET.

Due to the primary excitation of the donor, the same could in principle emit luminescent light. However, this is attenuated or nonexistent (quenched) by the energy transfer and can thus no longer be detected. Immediate changes in the donor substance that would normally be discovered immediately by its luminescent light can now be observed only indirectly through changes in the FERT effectiveness. As stated above, this depends from further factors (such as the donor-acceptor distance). The possibility to additionally observe the luminescent light from the donor would allow a distinction between the various effects. If, when practicing the present method, first a sample is pulsed or continuously irradiated with light ot the acceptor excitation wavelength, a saturation of the corresponding acceptor color markers, i.e. an excitation of most of those color markers, is obtained. A light pulse of a second wavelength (time deferred with respect to the light of the first wavelength, if the same is pulsed) excites the donor color marker which in turn indirectly excites the acceptor color marker through FRET. Since many of the acceptor color markers have already been excited (saturated) by the light of the first wavelength, the FRET excitation by the donor color marker is less. The inventive use of the pulsation of one of both wavelength ranges or the delay of the pulses of both wavelength ranges is advantageous in that less quenching of the luminescence of the donor color marker is effected. It is avoided that a large portion of the luminescent light of the donor color marker is invisible, since its excitation energy is used up by the FRET excitation of the acceptor color marker. By suitably selecting the temporal offset or the power of the light of the first wavelength, a different extent of saturation of the acceptor color marker is obtained, and thus an optimum suppression of the FRET quenching or the FRET signal is set.

A further possible application of the present method lies with an improved use of a FRET analysis employing FRET cascades. As indicated above, the effectiveness, and thus the observability of FRET, strongly decreases with the distance between donor and acceptor and disappears at a maximum distance (typically about 100 nm). In FRET cascades, a plurality of color markers is provided in a sample, so that this maximum possible distance can be increased. For example, a green color marker is excited by a green laser as the first donor (donor 1). Through FRET, the same excites a yellow color marker as the second donor (donor 2) which, through another FRET excitation, in turn excites a third, red color marker as an acceptor to emit luminescence signals. Thus, the distance variations between the donor 1 and the acceptor can be detected over an even larger region, since the energy transfer from donor 1 to the acceptor passes over donor 2 (FRET cascade) and, for example, the maximum distance can be used twice. A disadvantage of the method thus practiced is the insecurity whether a change in the acceptor luminescence signal has been caused by a change in the distance, and thus a FRET change, between donor 1 and donor 2, or by a change in the distance, and thus a FRET change, between donor 2 and the acceptor.

Using two temporal offset green and yellow pulsed light sources exciting only donor 1 or donor 2, respectively, the FRET effectivities and the distances between donor 1 and donor 2 can selectively be analyzed by the green laser and, for the donor 2 and the acceptor, by the yellow laser. Such, possibly even longer, FRET cascades are thus substantially improved by the use of electromagnetic radiation pulsed in at least one wavelength range.

In all fields of application of the invention, the possibility of varying the temporal offset of both laser pulses is advantageous. In this manner, a temporal offset optimal for the improvement of the measuring results (e.g. less photo destruction, more optimal cross-correlation, better signal-noise ratio) can be found. Moreover, it becomes possible, by systematic studies, i.e systematic changes in the temporal offset in different measurements, to characterize the mutual effects of processes and/or states (e.g. photo destruction, transient absorption, excited state of the color marker).

The present device serves to generate electromagnetic radiation pulsed in at least one wavelength range and/or one polarization. Preferably, a pulsating radiation is effected in at least two wavelength ranges and/or polarizations. Specifically, the device is constructed such, according to the invention, that the radiation pulses of the individual wavelength ranges and/or polarizations are temporally offset with regard to each other. Pulsating the at least one wavelength range and/or the at least one polarization is preferably effected such that at least two radiation pulses impinge on the color marker within the diffusion period in which a color marker diffuses through a measuring volume. The same is true for the other relative movement periods described before in connection with the method. The number of pulses and their length preferably correspond to the magnitudes described above with reference to the method. Such a device comprises a irradiation unit, a sample receiver, a detector unit and at least one optic unit.

The sample receiver serves to hold a chemical and/or biochemical sample containing at least one color marker in order to perform luminescence spectroscopy.

The detector unit serves to detect the radiation emitted by the sample. With the help of the optic units, the radiation is directed from the irradiation unit to the sample receiver and/or the radiation from the sample is directed to the detector unit.

The present device may be configured such that the light is directed from the irradiation unit to the sample receiver and the radiation from the sample is directed to the detector unit using the same optic unit, the same being arranged above or below the sample receiver. It is further possible to design the device such that the light from the irradiation unit is directed to the sample receiver by an optic unit located above the sample receiver and the radiation emitted by the sample is directed to the detector unit using another optic unit arranged below the sample receiver.

The irradiation unit configured according to the invention generates radiation in at least two different wavelength ranges and/or two different polarizations. Preferably, a laser unit is used as the irradiation unit. Here, two or more lasers are used, each producing laser light of another wavelength range and/or another polarization, at least one of the lasers being operated in a pulsed manner. The laser light pulses of the individual wavelength ranges and/or polarizations are mutually offset with regard to time, if, as preferred, a pulsation of both wavelength ranges or polarizations is effected. Thereby, as described above with reference to the present method, a significantly better measuring result is obtained.

Preferably, the laser unit comprises a control unit that is connected with one or all lasers. Here, a separate control unit may be provided for each individual laser, the individual control units being interconnected through a common control. Preferably, a single control unit is provided as a mode coupler for all lasers of the laser unit. A first laser is controlled through this control unit. The second and any further laser is preferably connected to the single control unit via a trigger wire. Because of the signal propagation times that depend on the length of the trigger wire, the laser light pulses, the laser light pulses of the second and any further laser can be delayed automatically with respect to those of the first laser. Other practical possibilities to obtain a delay between the lasers are path length differences between the different beam paths, or other electric components changing the signal propagation times.

The control unit of the present invention can preferably be constructed as described above with respect to the present method, so that, for example, a laser light pulse reaches the sample only when the excitation of a color marker, excited by the previous laser light pulse of a different wavelength range and/or another polarization, has substantially decayed. Further, the control unit allows for a control of the sequence of the individual lasers as well as of the time intervals between the laser light pulses.

In a preferred embodiment of the detector unit, the detector unit only comprises one combination detector connected to an evaluating unit. This single detector detects all luminescent light pulses given off by the individual color markers in the sample. Since the luminescent light pulses arrive at the detector with an offset in time, due to the delay of the radiation pulses exciting the color markers, the individual detected values can be attributed by the evaluating unit to the corresponding color markers and/or polarizations they come from. By combining the information on the sequence of the radiation pulses and the sequence of the detector signals in the evaluating unit, it is possible to sort the signals in red and green signals or parallel and perpendicularly polarized signals.

In another preferred embodiment, the detector unit comprises two detectors, one detector being for detecting the light emitted from the red color markers, the other being for detecting the light emitted from the green color markers. This ensures that no falsification of the results occurs due to errors by the evaluating unit. Further, the evaluating unit may be arranged in a simpler manner. When providing three or more color markers, the corresponding number of detectors can be provided.

In order to acquire additional information, the a polarizing beam splitter may be arranged downstream of the detectors. A light beam coming from a certain color marker is thus split into two beams of different polarization.

Further information on the sample, e.g. rotation properties, can be taken from these two beams. In particular, following the above described method, each of these detectors can measure different colors in succession. Thus, it is possible to measure more than one color in both polarizations using two detectors.

By gating, i.e. the synchronous turning off of a detector during a laser pulse, the measuring method may further be improved. Besides the already known suppression of prompt stray light and the resulting increase in the signal-noise ratio, the detection of the luminescence emission caused by a laser pulse can be suppressed specifically. When using a plurality of pulsed lasers of different wavelength ranges and/or different polarizations, this allows for a specific studying of transient states and processes.

Preferably, the device is designed as a high-precision confocal microscope. Preferably, the detecting unit comprises electronics with which to perform cross-correlation measurement, for example. The use of a confocal optical structure is preferred also because of the high resolution in the direction Z, i.e. along the optical axis, and of the good signal-noise ratio. However, any non-confocal optical measuring systems can be used for the practice of the present method.

When using the present device with differently polarized radiation and only one detector, the irradiation unit is preferably modified as follows:

(1) The radiation from a single non-polarized radiation source, such as a non-polarized laser, is split into two beams by a beam splitter which are polarized differently by a polarization filter and which are later on united again. The delay between the two differently polarized beams is realized by path length differences in the two beam paths.

(2) The radiation from a single non-polarized radiation source, such as a non-polarized laser, is split into two beams of different polarization by a polarizing beam splitter and afterwards united again. The delay between both differently polarized beams is obtained by path length differences in both beam paths.

(3) Generating two radiation pulses of different polarization using a single non-polarized radiation source can also be achieved with a fast rotating polarizing filter in a non-split beam path. Here, the speed of rotation of the polarizing filter is adjusted to the pulse frequency of the radiation source so that the individual radiation pulses alternately have a different polarization direction.

(4) Two polarized pulsed radiation sources of the same wavelength ranges but opposite polarizations are tuned to each other or triggered, as in the two-color approach, such that their pulses reach the sample successively with a delay.

Whereas all embodiments of the device have the advantage that only a single detector is required to register the differently polarized luminescent light portions, the embodiments (1)-(3) even require only a single pulsed radiation source.

The present invention, as described before with reference to the method, is advantageously developed especially by the suitable radiation device.

By coupling in two temporally offset radiation pulses of different wavelength ranges, e.g. red and green, and by using suitable optical filters, luminescent light of different wavelength ranges, e.g. read and green, can be detected separately and almost "simultaneously" with one detector, as described above. Thus, methods such as coincidence analysis or two-color cross-correlation measurement can be performed with only a single detector. This is not possible according to prior art.

With the present invention and the present device, the following measuring methods can be performed: spectrometry, multi-photon excitation (e.g. in two photon operation), laser scanning excitation, near field spectroscopy, Raman and Rayleigh scattered light applications, FIDA (fluorescence intensity distribution analysis) applications, two-dimensional FIDA applications, coincidence analysis and fluorescence life measurements. One may also use parallel confocal systems, such as Nipkow discs, line scanners, or PAM arrangements. Preferably, gated CCDs, CIDs, CMOSs or a plurality of CCDs, CIDs, or CMOSs are used that measure different signal portions through color splitters or polarizers.

With the present method it is also possible to measure changes in the conformation of a particle if the particle is marked with at least two markers and/or shows intrinsic luminescence at at least two locations (intrinsic markers). In particular, the particle is marked at defined locations with exactly two molecules. Here, the excitation is effected in alternating polarization. In an arrangement allowing the simultaneous detection of two colors and two polarization directions (for example, four detectors measuring the sample volume at the same time), the polarization of the two differently colored excitation pulses may be randomly polarized with respect to each other, as long as the ratio of the polarization directions is constant in time. This also includes changing polarization directions, as long as they occur periodically or quasi-periodically. When excitation photons hit the markers in a defined polarization direction, the absorption and thus the intensity of the emitted luminescence depends on the orientation of the markers with respect to each other. This dependence shows in the relationship between the respective detected polarizations. With fast rotating particles or particle portions or markers, an arrangement with four detectors, since otherwise the contributions from the two markers are mixed. Specifically, it is thus possible to track bistable states of molecular rotation axes, such as cis-trans rearrangements or chair rearrangements of ring structures. More complex applications of this method also include the breaking or the forming of cysteine bridges between protein units or folding leaflet arrangements. Specifically, the detection signal can be overlaid by luminescence life effects that can also be used for quantifying. In this application, it may be preferred to set the concentration of the sample such that, on average, less than one particle is in the measuring volume. It may also be preferred to fix the particles on a surface, for example, the surface of other particles, in particular nano particles, or on a planar surface, in particular in the form of arrays.

The present method further allows for a measurement of coded beads on the basis of particles referred to as "quantum dots" in prior art or similar particles. To this avail, different excitation wavelengths are emitted successively and the luminescence intensity or life of the particles is measured. Since the particles described could be adjusted exactly with respect to their luminescence properties, i.e. their excitation and emission wavelengths, for example, through size and material selection, it is possible by combining, e.g., three excitation colors, three emission colors and three luminescence lives to differentiate between two to the power of nine=512 particles. Thus, the particles described can be used directly without having to build combinations thereof into beads as is necessary in prior art systems.

Again, it may be preferred to set the concentration of the sample such that, on average, less than one particle is in a measuring volume. It may also be preferred to fix the particles on a surface, such as on that of other particles, in particular nano particles, or on a planar surface, in particular in the form of arrays.

The present method and the present device are particularly suitable for pharmaceutic active substance search (screening), for identifying and characterizing pharmaceutically relevant substances and molecules, for identifying analytes in diagnostic applications, for genome analysis or for cleaning and concentrating substrates.

The following is a detailed description of the invention with reference to test results and a preferred embodiment of the device. In the figures:

BRIEF DESCRIPTION OF THE SEVERAL VIEWS OF THE DRAWINGS

FIGS. 2-4 illustrate diagrams of the fluorescence intensities of a purely red color substance solution irradiated with a different light pulse delay of a red and a green laser, FIGS. 5-7 illustrate diagrams of the fluorescence decay in a red and a green detection channel in tests described with reference to FIGS. 2-4.

DETAILED DESCRIPTION OF THE INVENTION

Figure 1:
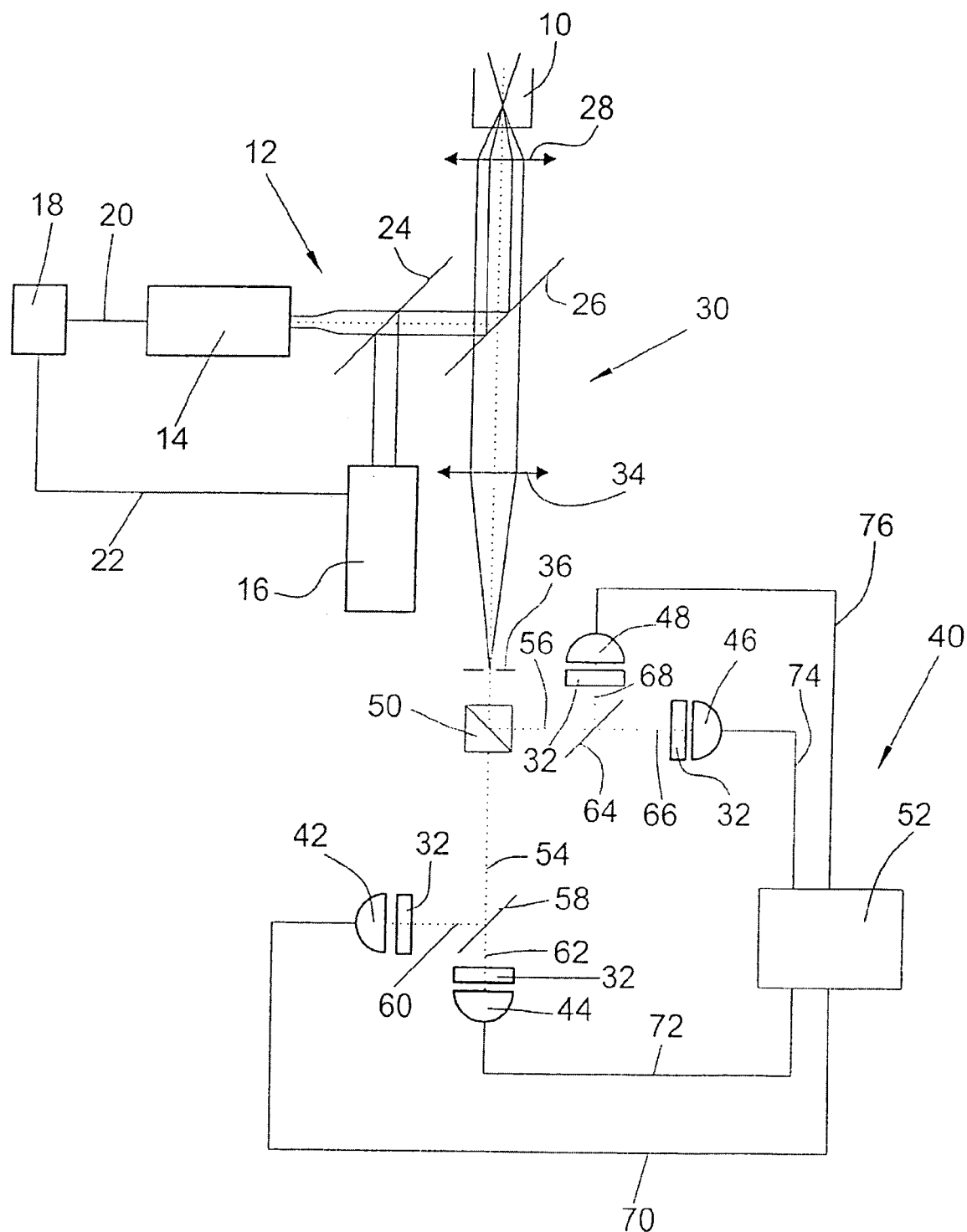
FIG. 1 schematically illustrates a preferred embodiment of the present device.

The preferred embodiment of the present device illustrated in FIG. 1 comprises a sample receiver 10. This sample receiver 10 is schematically illustrated as a single container holding the sample to be examined. The sample receiver may be micro- or nano-titer plates, for example. In the example shown, a laser unit 12 serving as the irradiation unit comprises an argon laser 14 generating green laser light with a wavelength of 496 nm. A second laser 16 is a red laser diode, generating laser light with a wavelength of 635 nm. Both lasers 14, 16 are operated in a rapid pulsed mode. When using the device of FIG. 1 to carry out the tests described in connection with FIGS. 2-8, the pulse frequency was 73 MHz.

The argon laser 14 is controlled through a mode coupler 18 connected to the argon laser 14 via a wire 20. Through the mode coupler, an exact pulse frequency is generated. The mode coupler 18 is further connected to the red laser diode 16 via a trigger wire 22. By providing the mode coupler as a common trigger unit, the pulse frequency of both lasers 14, 16 is identical. Due to the length of the trigger wire 22, the pulses generated by the two lasers 14, 16 are delayed with respect to each other. The delay is due to the signal propagation time of the control signals from the mode coupler 18 to the laser 16.

The light beams emitted by the two lasers 14, 16 are combined by a dichroitic beam splitter 24 so that they pass along an identical beam path. However, since the laser pulses are delayed with respect to each other, no overlapping of the individual pulses occurs. The laser light bundled by the dichroitic beam splitter 24 is directed towards the sample receiver 10 by a dichroitic mirror 26 and focused through an objective 28 into the sample held in the sample receiver 10.

The objective 28 and the dichroitic mirror 26 are already parts of an otic unit 30. The optic unit 30 further comprises a tube lens 34 and a pinhole diaphragm 36. The light emitted by the color markers contained in the sample passes through the objective 28, the dichroitic mirror 26 and the tube lens 34 by which it is focused on the pinhole diaphragm 36. This is a typical arrangement of a confocal microscope where portions of the light are canceled out by the pinhole diaphragm 36.

In the embodiment of the device illustrated, a detector unit 40 comprises four optical filters 32, four detectors 42, 44, 46, 48 as well as a polarizing beam splitter 50 and an evaluating unit 52. The beams passing the pinhole diaphragm 36 are split by the polarizing beam splitter 50 into a beam 54 with parallel polarized light and a beam 56 with perpendicularly polarized light. The beam 54 is split into two beams 60, 62 by a dichroitic beam splitter 58, one of the beams including the light given off by the red color marker and the other beam including the light given off by the green color marker.

Correspondingly, the other polarized beam 56 is split into a red and a green beam 66, 68 by a second dichroitic beam splitter 64, which are detected by the detectors 46 and 48, respectively. The optic filters 32 filter out edge portions of the emitted light, for example, which do not come from the color markers but, for example, from the material of the sample receiver 10. The beams 60, 62, 66, 68 detected by the detectors 42, 44, 46, 48 are transformed into electric signals and transferred to the evaluating unit 52 which typically is a PC adapted to the device. The evaluating unit determines the type of reaction that has occurred in the sample.

Instead of directing the laser light to the sample and to direct the light emitted from the sample to the detector unit using a single optic unit, two optic units may be used. The present device may be arranged such that the light from the irradiation unit to the sample receiver and the radiation emitted from the sample are directed to the detector unit using the same optic unit which may be located above or below the sample receiver. It is further possible to design the device such that the light from the irradiation unit is directed to the sample receiver by an optic unit located above the sample receiver, and that the radiation emitted from the sample is directed to the detector unit through another optic unit arranged below the sample receiver.

Instead of the irradiation unit with two lasers 14, 16 illustrated in FIG. 1, a irradiation unit with only a single light source may be used. To establish beam paths with two different wavelength ranges, a beam splitter is provided behind the light source, which decouples 50%, for example, of the light generated from the beam path, irrespective of the frequency of the light. This may be an inclined mirror, for example, that covers 50% of the beam path. Due to path length differences, a delay in time may be obtained between the two beam paths established. Here, only a single pulsed light source is required. To cause different wavelength ranges in both beam paths, a unit for changing the wavelength is provided in one of the beam paths. This may be a frequency doubling means or a frequency multiplier, for example. Further, an OPA may be provided. This is a non-linear crystal causing a frequency shift. Likewise, a Raman shifter may be provided to shift the wavelength range in one of the two beam paths.

A corresponding device with only a single light source may also be used when two beam paths with different polarizations are to act on the sample. Again, the beam path generated by the light source is split and a delay in the pulsed single light source is caused by the path length differences. To make a polarization change in one of the beam paths, a polarization filter is provided, for example, in the beam path as a unit for changing the polarization.

In the measurements depicted in FIGS. 2-7, a purely red color substance solution has always been examined. This is the color substance cyanin 5 (Cy5) dissolved in water in a concentration of 5 nM. The fluorescence life of Cy5 in water is 0.7 ns.

FIGS. 2-4 each illustrate the count rate of the detector over time. In all three tests, the sample was irradiated exclusively with the red laser within the first 5 s, with the red and the green laser in the time between 5s and 15 s, and again exclusively with the red laser between 15 and 20 s. in all three measurements, the frequency of the two pulsed lasers was 73 MHz.

In the measurement illustrated in FIG. 2, no pulse offset between the lasers was effected in range from 5-15 s win which both the red and the green laser were on. Thus, the read and green laser light pulses hit the sample and the red color marker simultaneously. It is obvious from the diagram (FIG. 2) that the count rate decreases largely in the range from 5-15 s. in those ranges, where the green laser was not on, i.e. in the range from 0-5 s and the range from 15-20 s, the count rate is significantly higher. This illustrates the destructive influence of the green laser on the red color markers.

In the measurement depicted in FIG. 3, a pulse offset between the red and the green laser of 2 ns was set in the time section from 5-15 s. the pulses from the green laser always occurred 2 ns after those of the red laser, the two laser light pulses alternately hitting the sample. As is obvious from the diagram (FIG. 3), the count rate in the range from 5-15 s is significantly higher than in the diagram of the measurement taken first (FIG. 2). Thus, even within a temporal offset of 2 ns, a certain decay of the excitation of the red color marker has occurred (about 94% for Cy5), so that a significantly lower number of red color markers has been destroyed by the green laser.

The effect of the present method is especially obvious from FIG. 4. In this measurement, a pulse offset of 10 ns was set in the range from 5-15 s. Here, the diagram shows no deviation of the count rate for the single ranges. Thus, it may be assumed that even after 10 ns approximately all previously excited red color markers have returned to their original state.

Figure 6:
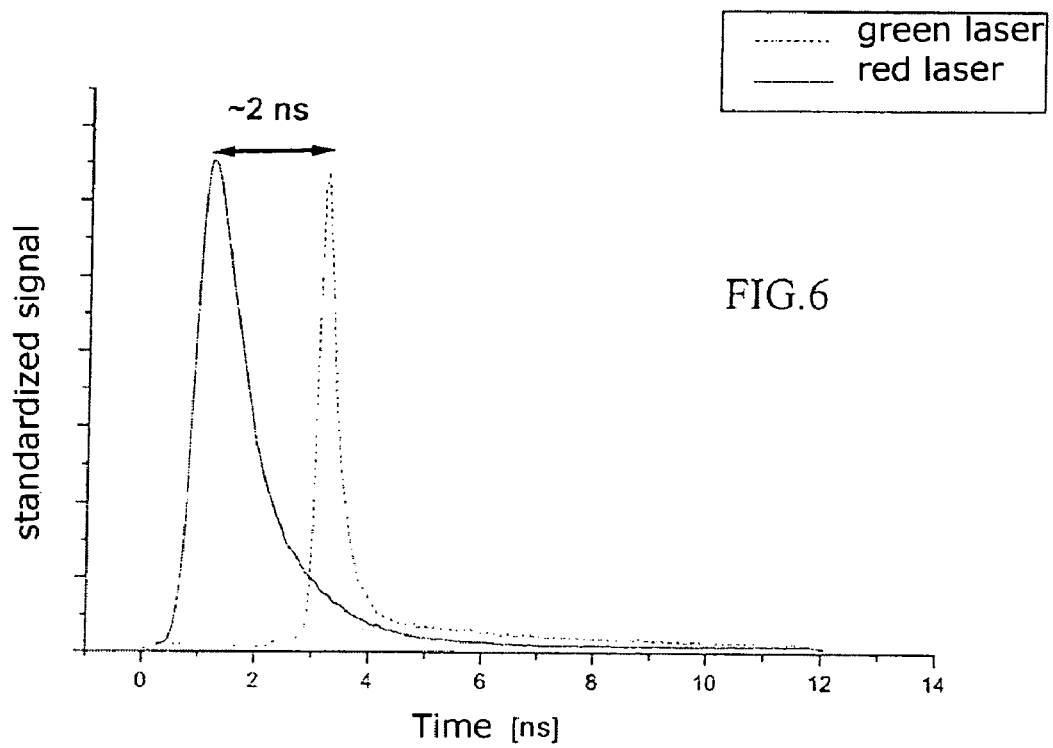
Figure 7:
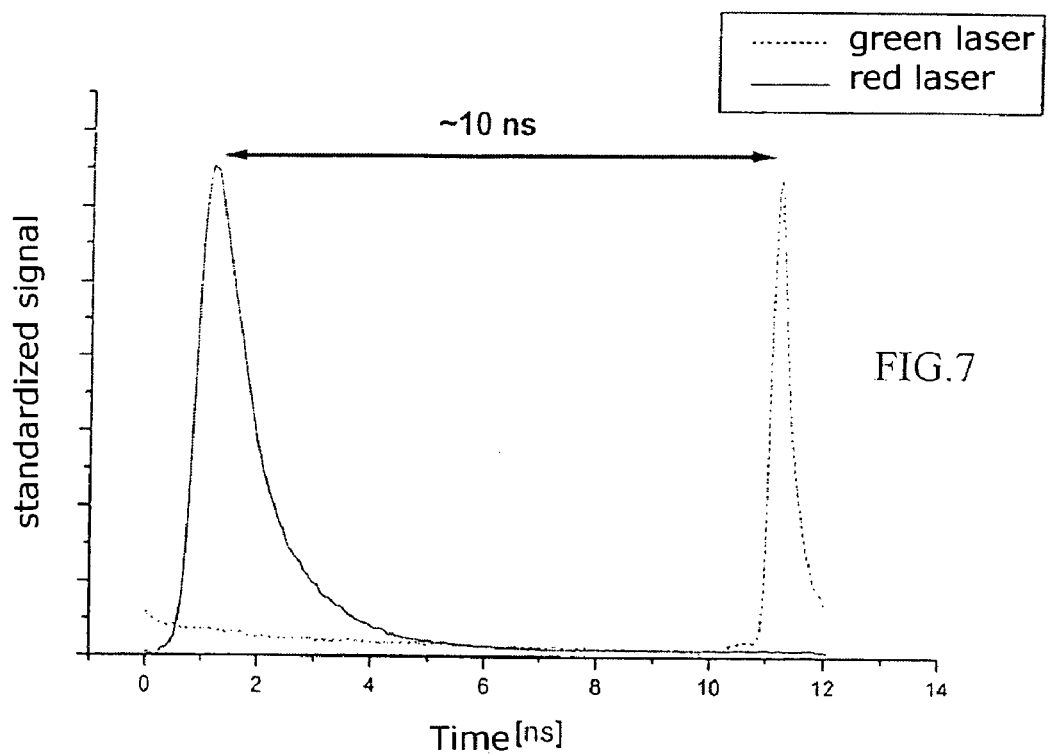

In FIGS. 5-7, the count rate of a red and a green detection channel is depicted over time. The detection channels are the corresponding detectors in connection with the evaluating unit. FIG. 5 corresponds to the measurement in FIG. 2, FIG. 6 corresponds to the measurement in FIG. 3, and FIG. 7 corresponds to the measurement in FIG. 4. The solid line represents the fluorescence caused by the red laser, while the broken line represents the fluorescence caused by the green laser. The measurements depicted in FIGS. 5-7 were made in the time from 5-15 s (FIGS. 2-4), i.e. when both lasers were on. In FIG. 5, there is no delay between the red and green laser light pulses, in FIG. 6, the delay is 2 ns as in FIG. 3, and in FIG. 7, the delay is 10 ns as in FIG. 4.

FIGS. 5-7 clearly show the shift of the maximum fluorescence signals of the red and the green detection channel with respect to each other, due to the pulse offset. With a pulse offset of 10 ns, the two detection channels can clearly be separated from each other. For example, this allows for the use of a single detector for both color markers, since it is known at which moment light signals from which color marker reach the detector.

Figure 8:
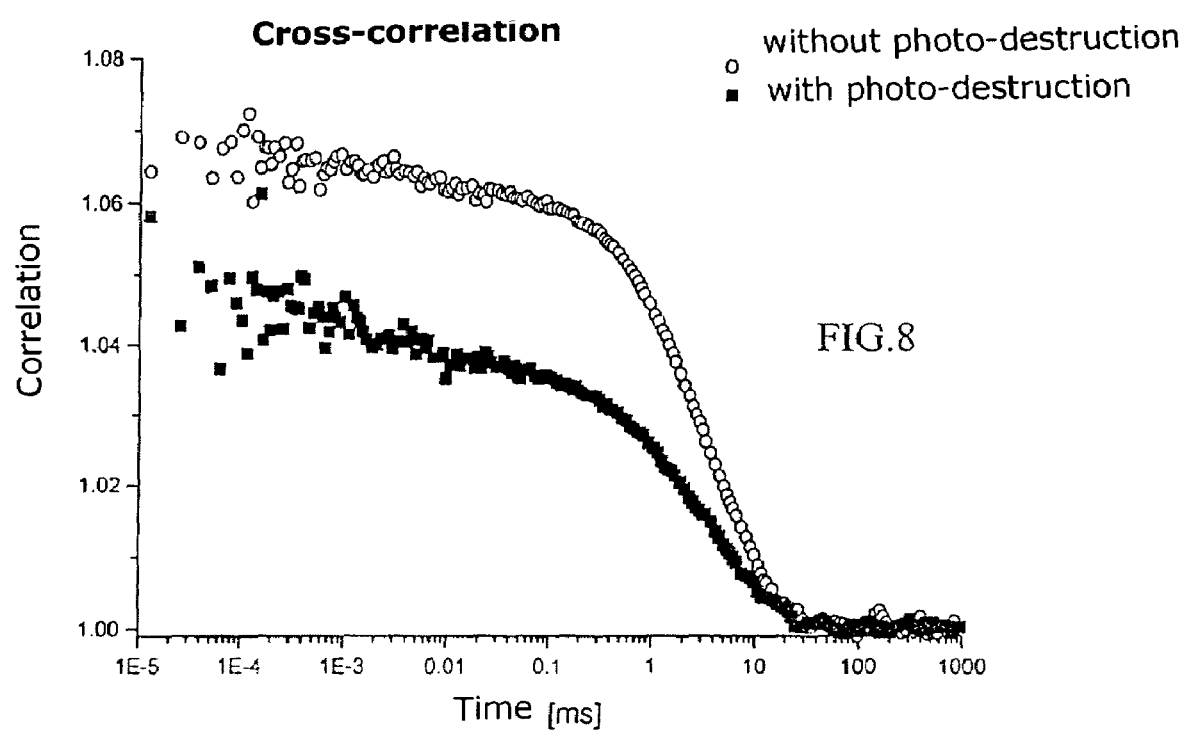
FIG. 8 shows a diagram in which the graph of cross-correlation measurements is illustrated.

The test illustrated in FIG. 8 is a measurement of a double-stranded oligo-nucleotide marked with Cy5 and rhodamine green, dissolved in water in a concentration of about 1 nM. The oligo-nucleotide has a length of 66 base pairs and prevents energy transfer because of the distance between the two color markers. A cross-correlation measurement of the red and green fluorescent light was performed. Again, the red and green lasers were pulsed and adapted to be shifted in time. The lower curve is the course of the cross-correlation for overlying laser light pulses, i.e. for laser light pulses without delay. In the upper curve, the laser light pulses were mutually offset. From equation 2, the upper curve yields a concentration, $C_{green+red}=1$ nM, of twice marked oligo-nucleotides, whereas the reduced amplitude of the lower curve leads to a lesser concentration, $C_{green+red}=0.6$ nM. Due to the pulse offset, no photo destruction occurs and the cross-correlation analysis leads to less falsified results.

The invention claimed is:

1. A method for measuring chemical and/or biological samples by means of spectroscopic or microscopic methods, wherein: the sample including at least one marker in a measuring volume is irradiated with electromagnetic radiation of at least two different wavelength ranges and/or polarizations, the excited marker emits radiation in an emission wavelength range, and the emitted radiation is detected by at least one detector, characterized in that the electromagnetic radiation used to excite the marker is pulsed in at least two different wavelength ranges and/or polarizations and the radiation pulses of the individual wavelength ranges and/or polarizations impinge on the sample with a temporal offset wherein a relative movement between the measuring volume and the marker, occurs in a relative movement period and the electromagnetic radiation used to excite the marker is pulsed in at least one wavelength range and/or one polarization such that at least two radiation pulses hit the marker within the relative movement period in which the measuring volume contains the marker.

2. The method of claim 1, wherein the relative movement between the measurement volume and the marker is a diffusion of the maker through the measuring volume during a diffusion period and the electromagnetic radiation used to excite the marker is pulsed in at least one wavelength range and/or one polarization such that at least two radiation pulses hit the marker within the diffusion period.

3. The method of claim 2, wherein the radiation of the individual wavelength ranges and/or polarizations is emitted in repetitive sequence.

4. The method of claim 2, wherein the sample includes two markers, each marker being excited by one wavelength range and/or one polarization, respectively.

5. The method of claim 2, wherein a red and/or a green color marker are used together with red and/or green excitation light, the green excitation light has a wavelength range of 480 to 550 nm and the red excitation light has a wavelength range of 630 to 690 nm.

6. The method of claim 1, wherein the marker is stationary and a the relative movement between the measuring volume and the marker occurs by moving the measuring volume and/or by moving the sample receiver containing the marker.

7. The method of claim 6, wherein the radiation of the individual wavelength ranges and/or polarizations is emitted in repetitive sequence.

8. The method of claim 6, wherein the sample includes two markers, each marker being excited by one wavelength range and/or one polarization, respectively.

9. The method of claim 6, wherein a red and/or a green color marker are used together with red and/or green excitation light, the green excitation light has a wavelength range of 480 to 550 nm and the red excitation light has a wavelength range of 630 to 690 nm.

10. The method of one of claim 1, wherein a radiation pulse is generated only after the excitation of the marker, excited by a previous radiation pulse of a different wavelength range and/or a different polarization, has substantially decayed.

11. The method of claim 10, wherein the radiation of the individual wavelength ranges and/or polarizations is emitted in repetitive sequence.

12. The method of claim 10, wherein the sample includes two markers, each marker being excited by one wavelength range and/or one polarization, respectively.

13. The method of claim 10, wherein a red and/or a green color marker are used together with red and/or green excitation light, the green excitation light has a wavelength range of 480 to 550 nm and the red excitation light has a wavelength range of 630 to 690 nm.

14. The method of claim 1, wherein the radiation of the individual wavelength ranges and/or polarizations is emitted in repetitive sequence.

15. The method of claim 1, wherein the sample includes two markers, each marker being excited by one wavelength range and/or one polarization, respectively.

16. The method claim 1, wherein a red and/or a green color marker are used together with red and/or green excitation light, the green excitation light has a wavelength range of 480 to 550 nm and the red excitation light has a wavelength range 630 to 690 nm.

17. The method of claim 16, wherein the green excitation light has a wavelength range of 485 to 535 nm.

18. The method of claim 17, wherein the red excitation light has a wavelength range of 635 to 655 nm.

19. The method of claim 1, wherein the marker has a characteristic fading time during which only it emits radiation, and the electromagnetic radiation used to excite the marker is pulsed in at least one wavelength range and/or one polarization such that at least two radiation pulses impinge on the marker within the fading period.

20. Device for measuring chemical and/or biological samples by means of spectroscopic or microscopic methods, comprising an irradiation unit for generating electromagnetic radiation in at least two different wavelength ranges and/or polarizations, a sample receiver for holding the sample including at least one marker, a detector unit comprising at least one detector for detecting the radiation emitted by the sample, and at least one optic unit directing the radiation from the irradiation unit to a measuring volume in the sample receiver and/or directing the radiation emitted by the sample to the detector unit, characterized in that the irradiation unit generates radiation pulsed in at least two different wavelength ranges and/or polarizations and the radiation pulses of the individual wavelength ranges and/or polarizations are temporally offset, wherein a relative movement between the measuring volume and the marker occurs in a relative movement period and the irradiation unit generates radiation that is pulsed such that at least two radiation pulses hit the marker within the relative movement period in which the measuring volume contains the marker.

21. The device of claim 20, wherein the marker diffuses through the measuring volume during a diffusion period and the irradiation unit generates radiation pulsed in at least one wavelength range and/or one polarization such that at least two radiation pulses hit the marker within the diffusion period.

22. The device of claim 20, wherein it comprises means for moving the measuring volume and/or the sample receiver containing the marker.

23. The device of claim 22, wherein the irradiation unit comprises a common control unit for all radiation sources.

24. The device of claim 23, wherein the control unit is connected to the radiation sources through a respective trigger wire, the time interval between the radiation pulses being defined by the length of the trigger wires.

25. The device of claim 20, wherein the irradiation unit is connected to a control unit for generating the radiation pulses.

26. The device of claim 25, wherein the control unit controls the radiation pulses such that a radiation pulse is generated only after the excitation of the marker, excited by a previous radiation pulse of a different wavelength range and/or a different polarization, has substantially decayed.

27. The device of claim 25, wherein the control unit controls the radiation pulses such that the radiation pulses of the individual wavelength ranges and/or polarizations are emitted in repetitive sequence.

28. The device of claim 25, wherein the control unit is a mode coupler.

29. The device of claim 20, wherein the irradiation unit comprises at least two radiation sources for generating different wavelength ranges and/or polarizations.

30. The device of claim 29, wherein the irradiation unit comprises two radiation sources, one radiation source generating red light and the other generating green light, and wherein the green light has a wavelength range 480 to 550 nm and the red light has a wavelength range 630 to 690 nm.

31. The device of claim 30, wherein the green light has a wavelength range of 485 to 535 nm.

32. The device of claim 31, wherein the red light has a wavelength range of 635 to 655 nm.

33. The device of claim 20, wherein the irradiation unit comprises only one non-polarized pulsed radiation source, the irradiation unit additionally comprising (a) a beam splitter and, in each beam path established, a polarizing filter as well as a component for combining the beam paths, or (b) a polarizing beam splitter for establishing two beam paths of different polarizations as well as a component for combining the beam paths, or (c) a rapidly rotating polarizing filter in an unsplit beam path.

34. The device of claim 20, wherein the irradiation unit comprises two polarized pulsed radiation sources of the same wavelength range but of opposite polarization.

35. The device of claim 20, wherein the detector unit comprises only one combination detector connected to an evaluating unit, the evaluating unit evaluating the radiation emitted by the at least one marker separately due to the time interval.

36. The device of claim 20, wherein the detector unit comprises two detectors.

37. The device of claim 20, wherein the detector unit comprises a beam splitter, arranged before the detectors, for generating two beams of different polarization and each beam is detected by at least one detector.

38. The device of claim 20, wherein the marker has a characteristic fading time during which only it emits radiation, and the irradiation unit generates radiation that is pulsed in at least one wavelength range and/or polarization such that at least two radiation pulses hit the marker within the fading period.

* * * * *